US010172717B2

(12) United States Patent
Hansell (10) Patent No.: US 10,172,717 B2
(45) Date of Patent: *Jan. 8, 2019

(54) ARTIFICIAL DISC

(71) Applicant: GLOBUS MEDICAL, INC., Audubon, PA (US)

(72) Inventor: Noah Hansell, King of Prussia, PA (US)

(73) Assignee: GLOBUS MEDICAL, INC., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/260,466

(22) Filed: Sep. 9, 2016

(65) Prior Publication Data

US 2016/0374827 A1     Dec. 29, 2016

Related U.S. Application Data

(63) Continuation of application No. 14/070,171, filed on Nov. 1, 2013, now Pat. No. 9,463,095, which is a
(Continued)

(51) Int. Cl.
*A61F 2/44*     (2006.01)
*A61F 2/30*     (2006.01)

(52) U.S. Cl.
CPC ............ *A61F 2/4425* (2013.01); *A61F 2/442* (2013.01); *A61F 2002/30014* (2013.01); *A61F 2002/30069* (2013.01); *A61F 2002/30225* (2013.01); *A61F 2002/30228* (2013.01); *A61F 2002/30331* (2013.01); *A61F 2002/30354* (2013.01); *A61F 2002/30538* (2013.01); *A61F 2002/30556* (2013.01); *A61F 2002/30563* (2013.01);
(Continued)

(58) Field of Classification Search
CPC .. A61F 2/442; A61F 2/4425; A61F 2002/443; A61F 2002/4435; A61F 2002/444
USPC ................................ 606/246, 248, 249, 279; 623/17.11–17.16
See application file for complete search history.

(56) References Cited

U.S. PATENT DOCUMENTS 8,287,598 B1     10/2012 Doty
8,303,879 B2 *   11/2012 Bertele .................... A61F 2/446
                                                           264/273
(Continued)

FOREIGN PATENT DOCUMENTS

WO     2004052234 A2     6/2004
WO     2010147795 A2     12/2010

*Primary Examiner* — Julianna N Harvey
*Assistant Examiner* — Christina Negrellirodrigue (57) ABSTRACT

A medical device includes a base ring configured to be implanted within a body of a patient. The base ring provides a contact surface to a vertebra. Multiple layers of multiple leveling plates are configured to equalize forces applied to the contact surface of the base ring, where at least one of the layers of the leveling plates engages an inner surface of the base ring. A layer of multiple pads is included with a top surface of the pads configured to maintain a parallel plane and a bottom surface of each of the multiple pads is configured to engage a top surface of one of the layers of the leveling plates. A cover is configured to enclose the multiple layers of the leveling plates, the layer of the multiple pads and the base ring. The cover provides a contact surface to a vertebra.

18 Claims, 10 Drawing Sheets

Related U.S. Application Data continuation of application No. 13/421,121, filed on Mar. 15, 2012, now Pat. No. 8,597,355.

(52) U.S. Cl.
CPC .............. *A61F 2002/30607* (2013.01); *A61F 2002/30616* (2013.01); *A61F 2002/443* (2013.01); *A61F 2310/00017* (2013.01); *A61F 2310/00023* (2013.01)

(56) References Cited

U.S. PATENT DOCUMENTS

| | | |
|---|---|---|
| 8,685,101 B2 | 4/2014 | Kraft et al. |
| 2007/0067038 A1 | 3/2007 | Studer et al. |
| 2008/0319548 A1 | 12/2008 | Kuras et al. |
| 2010/0030335 A1 | 2/2010 | Arramon |
| 2010/0312347 A1 | 12/2010 | Arramon et al. |
| 2010/0324688 A1* | 12/2010 | Doty .................... A61F 2/4425 623/17.16 |
| 2011/0071635 A1 | 3/2011 | Zhang et al. |

\* cited by examiner

FIG. 14 ań# ARTIFICIAL DISC

CROSS-REFERENCE TO RELATED APPLICATIONS

This patent application is a continuation application of U.S. patent application Ser. No. 14/070,171 filed on Nov. 1, 2013, which is a continuation application of U.S. patent application Ser. No. 13/421,121 filed on Mar. 15, 2012 (now issued as U.S. Pat. No. 8,597,355), both of which are incorporated in their entirety herein by reference.

TECHNICAL FIELD

This description relates to medical devices and more particularly to an artificial (or prosthetic) disc configured to be coupled to a portion of the spine.

BACKGROUND

A variety of medical devices and medical device systems may be implanted within a body of a patient to provide support to a portion or portions of the patient's body. For example, some medical devices may be implanted and coupled to backbones or portions of a spine of a patient and may be configured to provide support to the spinal bone structure of the patient.

When a vertebra of a patient is traumatized (e.g., damaged or diseased), a need for surgery may arise to replace and/or repair the traumatized vertebra.

SUMMARY

According to one general aspect, a medical device includes a base ring configured to be implanted within a body of a patient. The base ring provides a contact surface to a vertebra. The medical device includes multiple lower leveling plates having a non-flat bottom surface. The non-flat bottom surface of each of the multiple lower leveling plates engages an inner surface of the base ring and each of the multiple lower leveling plates is held in place within the base ring by a member extending from the base ring through a bore in the lower leveling plate. Multiple upper leveling plates have a bottom surface. The bottom surface of each of the multiple upper leveling plates engage a top surface of the multiple lower leveling plates and each of the multiple upper leveling plates is held in place within the base ring by a member extending through the upper leveling plate and engaging bores in the base ring. Multiple pads have a top surface and a bottom surface. The top surfaces of the multiple pads are arranged and configured to maintain a parallel plane and the bottom surface of each of the multiple pads engage the top surface of the upper leveling plates. A cover is configured to enclose the multiple lower leveling plates, the multiple upper leveling plates, the multiple pads and the base ring. The cover provides a contact surface to a vertebra. A compressible member is arranged through a center of the multiple lower leveling plates, the multiple upper leveling plates and the multiple pads and the compressible member has a top surface that engages the cover.

Implementations may include one or more of the following features. For example, the base ring may define a disc shape and the base ring may define a space between an inner wall and an outer wall. The space between the inner wall and the outer wall is configured to receive the multiple lower leveling plates and the multiple upper leveling plates. The inner wall of the base ring defines an area to receive the compressible member. A top of the outer wall of the base ring defines multiple areas to receive the multiple pads.

The multiple lower leveling plates and the multiple upper leveling plates are configured to equalize and distribute forces applied to the contact surface of the base ring with the vertebrae and the contact surface of the cover with the vertebrae. The multiple pads maintain the parallel plane using the multiple lower leveling plates and the multiple upper leveling plates. The non-flat bottom surface of the lower leveling plates is defined by a first flat area contouring to a sloped round area contouring to a second flat area. Each of the multiple lower leveling plates may be symmetrical about its center. The bore in each of the multiple lower leveling plates may extend through a center of the lower leveling plate from the top surface to the bottom surface. The top surface of each of the multiple pads may be flat and the bottom surface of each of the multiple pads may define a platform having a raised spherical member on a top surface of the platform. The cover may define a circumferential wall having a lip at a top of the circumferential wall. The compressible member is contained within a diameter defined by an inner wall of the base ring. The compressible member may be a biocompatible, flexible material.

In another general aspect, a medical device includes a base ring configured to be implanted within a body of a patient. The base ring provides a contact surface to a vertebra. Multiple layers of multiple leveling plates are configured to equalize forces applied to the contact surface of the base ring, where at least one of the layers of the leveling plates engages an inner surface of the base ring. A layer of multiple pads is included with a top surface of the pads configured to maintain a parallel plane and a bottom surface of each of the multiple pads is configured to engage a top surface of one of the layers of the leveling plates. A cover is configured to enclose the multiple layers of the leveling plates, the layer of the multiple pads and the base ring. The cover provides a contact surface to a vertebra.

Implementations may include one or more of the following features. For example, the medical device may include a compressible member arranged through a center of the multiple layers of the multiple leveling plates and the multiple pads. The compressible member may be contained within a diameter defined by an inner wall of the base ring and the compressible member may have a top surface that engages the cover.

The multiple layers of multiple leveling plates may include a layer of multiple lower leveling plates having a non-flat bottom surface that is arranged circumferentially inside the base ring. The non-flat bottom surface of each of the multiple lower leveling plates may engage the inner surface of the base ring. The multiple layers may include a layer of multiple upper leveling plates having a bottom surface that is arranged circumferentially inside the base ring. The bottom surface of each of the multiple upper leveling plates engages a top surface of the multiple lower leveling plates. The multiple pads may maintain the parallel plane using the multiple lower leveling plates and the multiple upper leveling plates. The top surface of each of the multiple pads may be flat and the bottom surface of each of the multiple pads may define a platform having a raised spherical member on a top surface of the platform.

In another general aspect, a method includes inserting a prosthetic disc into a portion of an anatomical structure within a body of a patient. The prosthetic disc includes a base ring, multiple layers of multiple leveling plates configured to equalize forces applied to a contact surface of the base ring and a layer of multiple pads with each of the pads having a top surface and a bottom surface. The top surface of the pads is configured to maintain a parallel plane and the bottom surface of each of the multiple pads engages a top surface of one of the layers of the leveling plates. A cover is configured to enclose the multiple layers of the leveling plates, the layer of the multiple pads and the base ring. The method includes contacting an outer surface of the base ring to a vertebrae and contacting an outer surface of the cover to a vertebrae.

Implementations may include one or more of the following features. For example, the prosthetic disc may include a compressible member arranged through a center of the multiple layers of the multiple leveling plates and the multiple pads. The compressible member may be contained within a diameter defined by an inner wall of the base ring and the compressible member may have a top surface engaging the cover.

The details of one or more implementations are set forth in the accompanying drawings and the description below. Other features will be apparent from the description and drawings, and from the claims.

DETAILED DESCRIPTION

The devices and methods described herein are generally directed to medical devices that can be used to support, stabilize and/or replace anatomical structures within a body of a patient. In some implementations, the devices and methods described herein are configured to provide support to a spine or back of a patient, including providing support between two vertebrae in the spine or back of the patient. In other implementations, other portions of the body of the patient can be supported by the devices described herein.

The medical devices described herein (also referred to as "apparatus" or "device") may be used as a prosthetic or artificial disc within a body of a patient. The terms "prosthetic" and "artificial" may be used interchangeably throughout this document to mean the same thing. The medical devices described herein may be implanted within a body of a patient to assist in maintaining normal physiologic motion in the spine of the patient.

Figure 1:
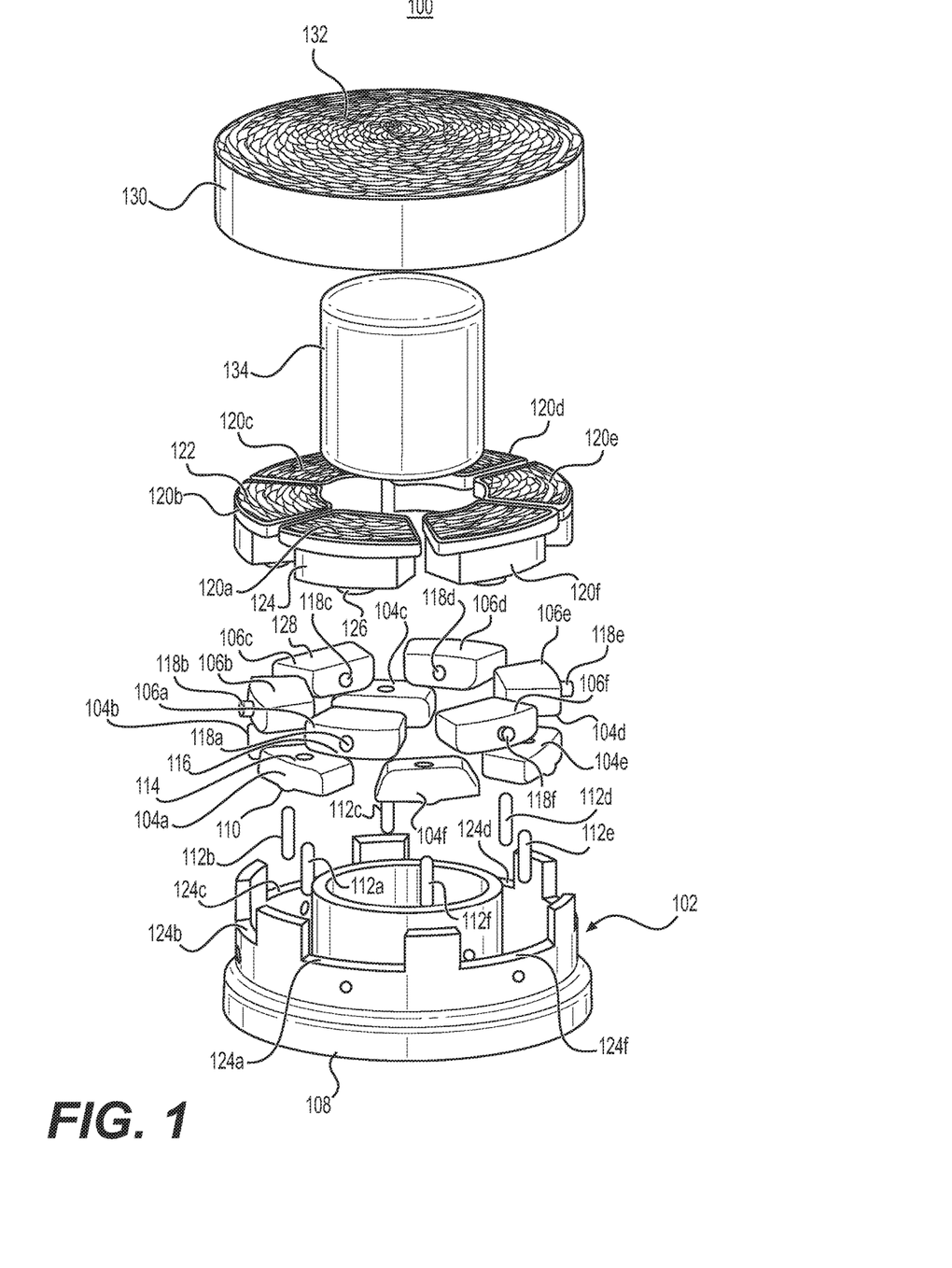
FIG. 1 is an exploded view of a medical device according to an exemplary implementation.

FIG. 1 illustrates an exploded view of a medical device 100, according to an exemplary implementation. The medical device 100 includes a base ring 102, a layer of multiple lower leveling plates 104a-104f and a layer of multiple upper leveling plates 106a-106f. The base ring 102 may provide a contact surface 108 to a vertebra in a spine of a patient. For example, the base ring 102 may provide a contact surface 108 to mate to the superior endplate of the inferior vertebra within a patient. The multiple lower leveling plates 104a-104f and the multiple upper leveling plates 106a-106f may work together to equally distribute the forces applied to the medical device 100. In this manner, the forces may be equalized and distributed all over an entire surface using the lower leveling plates 104a-104f and the upper leveling plates 106a-106f.

The lower leveling plates 104a-104f include a non-flat or non-planar bottom surface 110 that engages an inner surface of the base ring 102. Each of the lower leveling plates 104a-104f may be held in place within the base ring 102 by a corresponding support member 112a-112f. In one exemplary implementation, the support members (or members) 112a-112f may be dowels. The members 112a-112f may be received into openings or bores on the inner surface of the base ring 102 and extend vertically from the base ring 102 through a bore in each of the lower leveling plates 104a-104f. The non-flat bottom surface 110 on each of the lower leveling plates 104a-104f may cause the lower leveling plates 104a-104f to rock when a force is applied to the top surface 114 of the lower leveling plates 104a-104f by a bottom surface 116 of the upper leveling plates 106a-106f.

The upper leveling plates 106a-106f may be layered to contact the top surfaces 114 of the lower leveling plates 104a-104f. Each of the upper leveling plates 106a-106f may be held in place within the base ring 102 by a corresponding support member 118a-118f that extends horizontally through a bore in the upper leveling plates 106a-106f and engages bores in the base ring 102. In one exemplary implementation, the corresponding support members 118a-118f may be dowels. The dowels allow movement of the upper leveling plates 106a-106f, including movement that pivots the upper leveling plates 106a-106f about the dowel.

Figure 2:
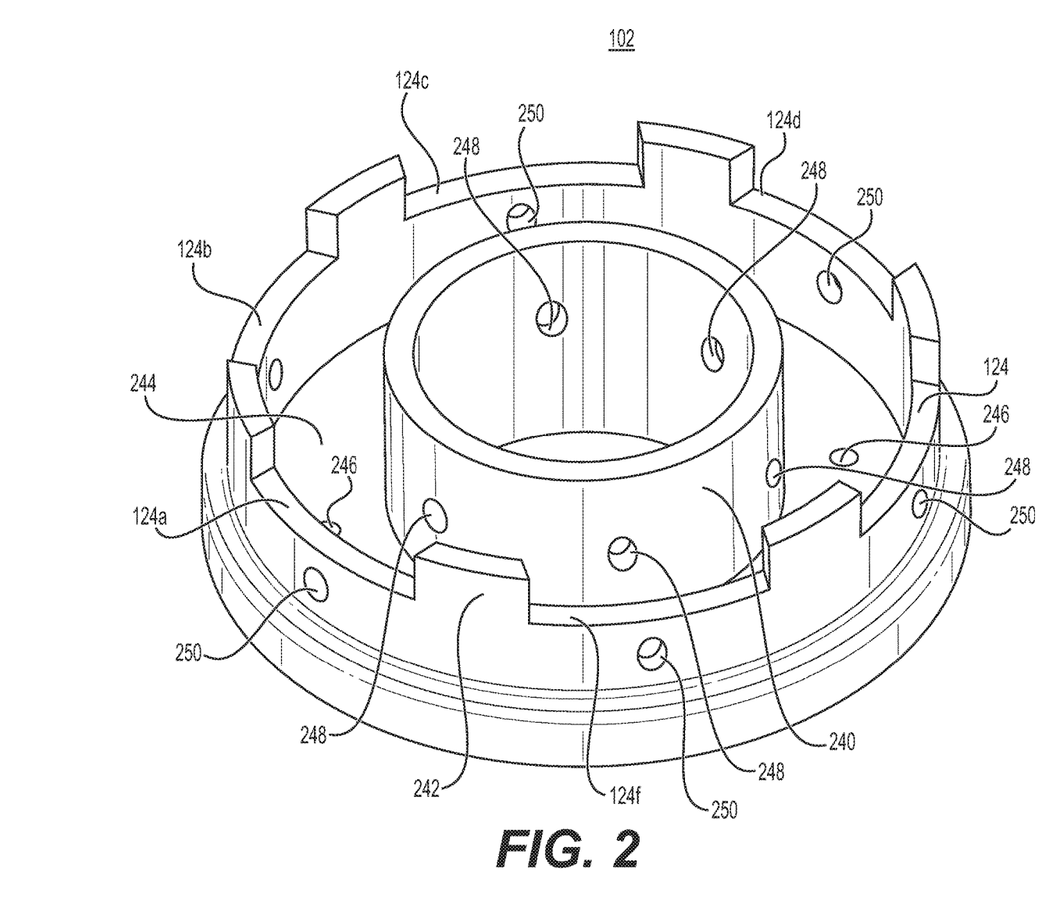
FIG. 2 is a perspective view of a base ring of the medical device of FIG. 1.

In this exemplary implementation, the medical device 100 includes six (6) lower leveling plates 104a-104f and six (6) upper leveling plates 106a-106f. In one exemplary implementation, the lower leveling plates 104a-104f are offset from the upper leveling plates 106a-106f, based on the spacing and location of the bores in the base ring 102 (as illustrated in FIG. 2 and described in more detail below). In other exemplary implementations, the bores in the base ring 102 may be located in other positions such that the each of the upper leveling plates 106a-106f lines up directly on top of one of the lower leveling plates 104a-104f.

In other exemplary implementations, the number of lower leveling plates 104a-104f and the number of upper leveling plates 106a-106f may vary depending on a size of the base ring 102 and/or on a size of the leveling plates themselves. While the size of each of the lower leveling plates 104a-104f is illustrated in this example is uniform or the same, other exemplary implementations may include different lower leveling plates 104a-104f with non-uniform sizes or sizes that are different from each other. Similarly, while the size of each of the upper leveling plates 106a-106f is illustrated in this example as uniform or the same, other exemplary implementations may include upper leveling plates 106a-106f with non-uniform sizes or sizes that are different from each other.

In other exemplary implementations, the number of lower leveling plates 104a-104f and upper leveling plates 106a-106f may not be a one-to-one correspondence. For example, in one exemplary implementation, there may be more lower leveling plates 104a-104f than upper leveling plates 106a-106f. Alternatively, in another exemplary implementation, there may be more upper leveling plates 106a-106f than lower leveling plates 104a-104f. The variation in the number of lower leveling plates 104a-104f and upper leveling plates 106a-106f may be due, at least in part, on the size of the leveling plates and/or the size of the base ring 102.

The medical device 100 includes a layer of multiple pads 120a-120f. The pads 120a-120f may be arranged circumferentially around the base ring 102. The base ring 102 may define multiple areas 124a-124f to receive the multiple pads 120a-120f. Each of the pads 120a-120f may include a generally flat top surface 122 and a bottom surface that includes a platform area 124 having a raised spherical member 126. The top surface 122 of the pads 120a-120f may be configured to maintain a parallel plane. The bottom surface having the platform area 124 and the raised spherical member 126 may engage a top surface 128 of each of the upper leveling plates 106a-106f.

The top surfaces 122 of all of the pads 120a-120f may maintain a parallel plane across the top surfaces based on the equalizing motion of the upper leveling plates 106a-106f and the lower leveling plates 104a-104f. While this exemplary implementation illustrates six (6) pads 120a-120f, other exemplary implementations may use a different number of pads based on, for example, a size of the pad and/or a size of the medical device 100, including a size of the base ring 102.

The medical device 100 includes a cover 130 that is configured to enclose the lower leveling plates 104a-104f, the upper leveling plates 106a-106f, the pads 120a-120f and the base ring 120. The cover 130 and the base ring 102 may be configured to hold the assembly together. The cover 130 includes a contact surface 132 configured to contact a vertebra. The contact surface 108 of the base ring 102 and the contact surface 132 of the cover 130 may include a plasma layer, for example in the form of a spray, on the surface.

The medical device 100 includes a compressible member 134 that is a cylindrical-shaped member that is arranged through a center of the lower leveling plates 104a-104f, the upper leveling plates 106a-106f and the pads 120a-120f. The compressible member 134 also may be referred to as a cushion. The compressible member 134 may be a shock dampening component that is made of or includes materials that are flexible and soft and that provide a shock dampening effect when forces are applied to the medical device 100.

For example, the compressible member 134 may be a soft polycarbonate-urethane (PCU), rubber, silicone or any other flexible soft material that is biocompatible. The base ring 102 may define an area to receive the compressible member 134 and the compressible member 134 may be constrained within the area defined by the base ring 102.

In one exemplary implementation, the compressible member 134 may be slightly longer than the rest of the assembly. As force is exerted between the vertebras of the spine causing compression between the base ring 102 and the cover 130, the soft compressible member 134 would try to expand radially. Since the compressible member 134 is contained within a fixed radial area defined by the base ring 102, the compressible member 134 would become more rigid and thus absorb shock forces well.

Referring also to FIG. 2, a perspective view of the base ring 102 of FIG. 1 is illustrated. The base ring 102 may define a spherical or disc shape. The base ring 102 may define an inner wall 240 and an outer wall 242. The inner wall may define an opening through which the compressible member 134 passes through. A diameter of the opening may constrain the compressible member 134.

The inner wall 240 and the outer wall 242 may define an area, including an inner surface 244, that is configured to receive the lower leveling plates 104a-104f and the upper leveling plates 106a-106f on top of the lower leveling plates 104a-104f. The inner surface 244 may engage the non-flat bottom surface 110 of the lower leveling plates 104a-104f. The inner surface 244 may include multiple bores 246 that are configured to receive the members 112a-112f that hold the lower leveling plates 104a-104f in position within the base ring 102.

The inner wall 240 may include multiple bores 248 and the outer wall 242 may include multiple corresponding bores 250 through which the members 118a-118f may extend through to hold the upper leveling plates 106a-106f in position within the base ring 102.

The top of the outer wall 242 may include multiple areas 124a-124f or cut outs of the top wall 242 that are configured to receive the pads 120a-120f. The areas 124a-124f may be sized to receive the pads 120a-120f such that the sides of the pads 120a-120f abut to form a continuous top surface across all of the pads 120a-120f.

Figure 3:
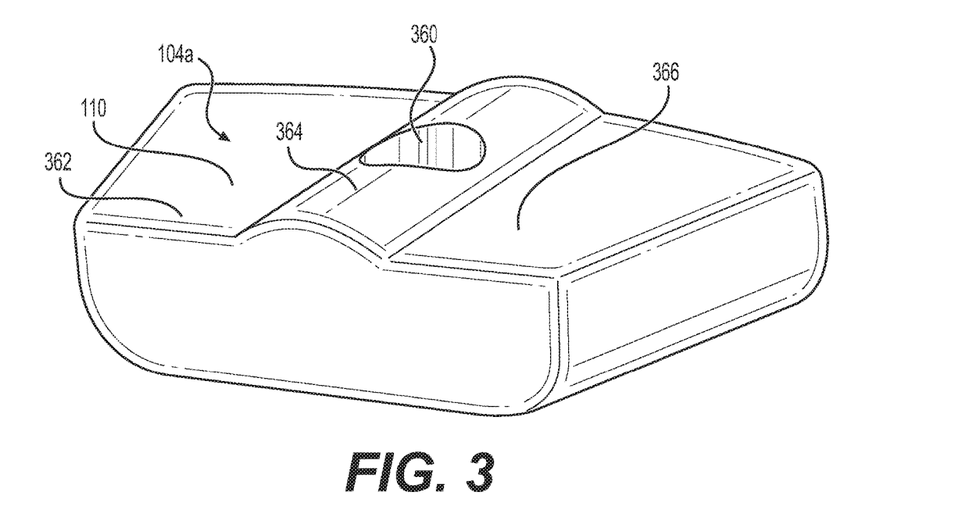
FIG. 3 is a perspective view of a lower leveling plate illustrating a bottom surface of the lower leveling plate of the medical device of FIG. 1.
Figure 4:
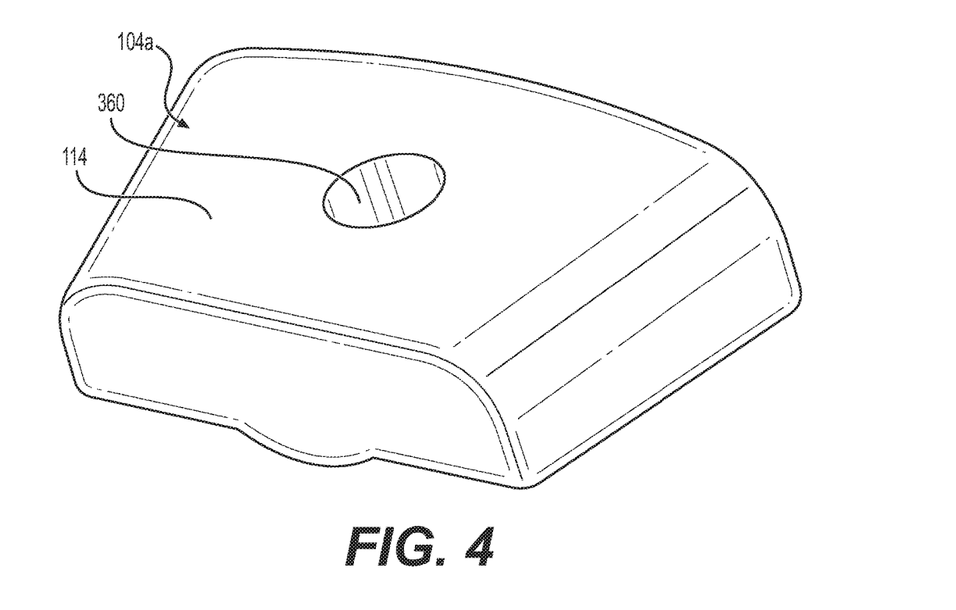
FIG. 4 is a perspective view of a lower leveling plate illustrating a top surface of the lower leveling plate of the medical device of FIG. 1.

Referring also to FIGS. 3 and 4, a perspective view illustrates a bottom surface 110 of a lower leveling plate 104a (FIG. 3) and a perspective view illustrates a top surface 114 of a lower leveling plate 104a (FIG. 4). The lower leveling plate includes a bore 360 there through. The bore 360 may extend through the center of the lower leveling plate 104a from the top surface 114 to the bottom surface 110. The bore 360 is sized to receive the member 112a to hold the lower leveling plate 104a in position within the base ring 102. The lower leveling plate 104a is symmetrical about its center, where the bore 360 may define the center of the plate.

As described above the bottom surface 110 of the lower leveling plate 104a is a non-flat or non-planar surface. The bottom surface 110 may engage the inner surface 244 of the base ring 102 and rock on the inner surface 244 based on the forces applied to the top surface 114 of the lower leveling plate 104a. The bottom surface 110 may include a first generally flat area 362 that contours to a sloped area 364 and then contours to a second flat area 366. The sloped area 364 may form a hump on the otherwise generally flat bottom surface 110. The hump allows the lower leveling plate 104a to rock when forced by one or more of the upper leveling plates 106a-106f.

The top surface 114 of the lower leveling plate 104a is generally flat across the top. The top surface 114 may be round at the edges and the generally flat area may round slightly downward. The top surface 114 may engage a bottom surface 116 of one or more of the upper leveling plates 106a-106f.

Figure 5:
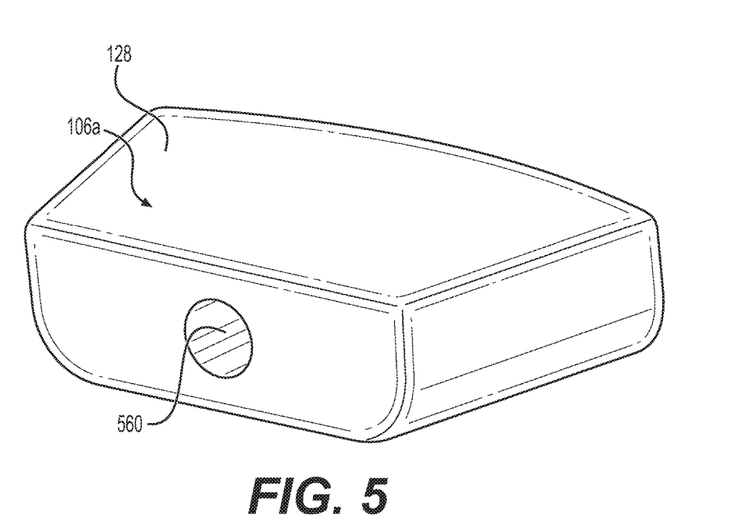
FIG. 5 is a perspective view of an upper leveling plate illustrating a top surface of the upper leveling plate of the medical device of FIG. 1.
Figure 6:
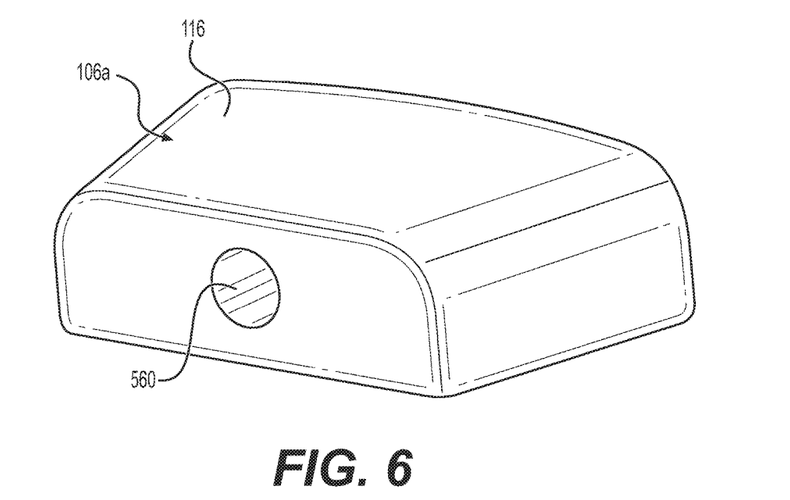
FIG. 6 is a perspective view of an upper leveling plate illustrating a bottom surface of the upper leveling plate of the medical device of FIG. 1.

Referring also to FIGS. 5 and 6, a perspective view illustrates a top surface 128 of an upper leveling plate 106a (FIG. 5) and a perspective view illustrates a bottom surface 116 of an upper leveling plate 106a (FIG. 6). The upper leveling plate 106a includes a horizontal bore 560 through its center. The bore 560 is configured to receive a member 118a that holds the upper leveling plate 106a in position within the base ring 102. When the upper leveling plate 106a is positioned in the base ring 102, the bore 560 is lined up with the corresponding bores 248 and 250 on the base ring 102 and the member 118a is received through the bores 248, 250 and 560 to hold the upper leveling plate 106a in position. The upper leveling plate 106a may pivot about its center on the member 118a as forces are applied from one or more pads 120a-120f and, in turn, may apply forces to one or more lower leveling plates 104a-104f.

The bottom surface 116 is configured to engage a top surface 114 of one or more lower leveling plates 104a-104f. The bottom surface 116 is generally flat or planar with rounded edges. The top surface 128 is generally flat and is configured to engage a bottom surface of one or more of the pads 120a-120f. As can be seen from FIGS. 3-6, the lower leveling plate 104a and the upper leveling plate 106a, are shaped and contoured to fit circumferentially around the base ring 102.

Figure 7:
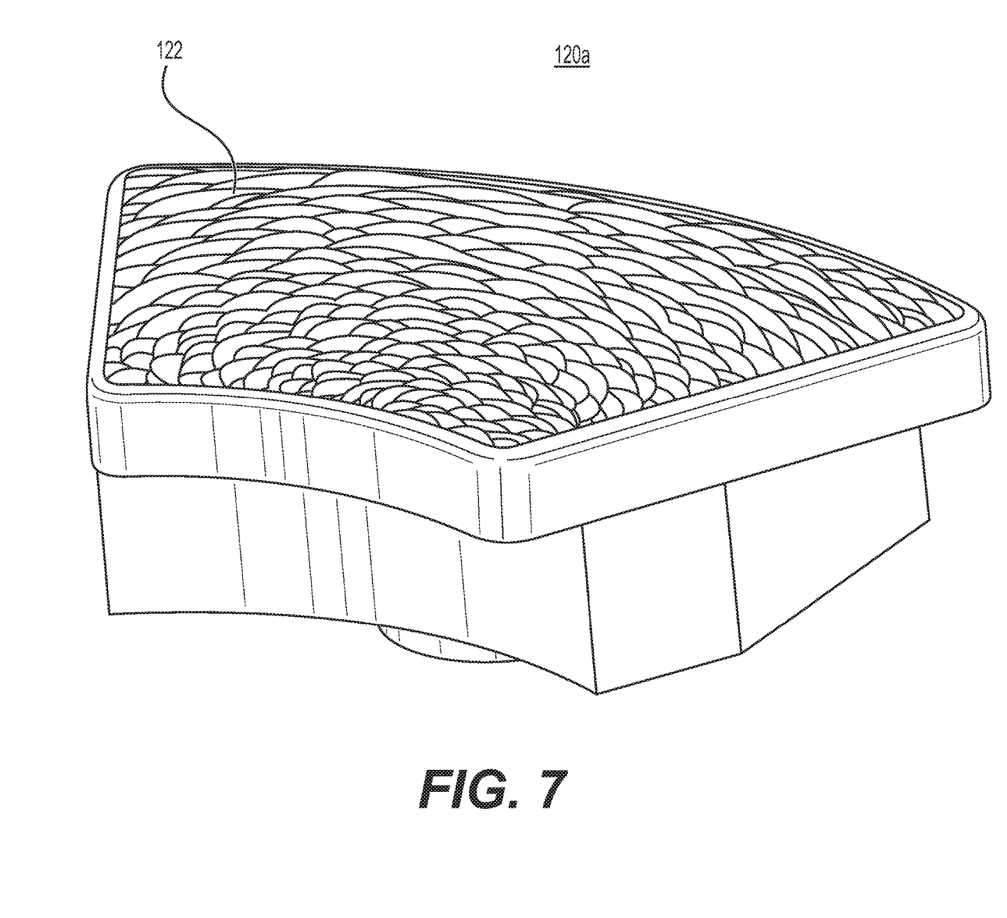
FIG. 7 is a perspective view of a pad illustrating a top surface of the pad of the medical device of FIG. 1.
Figure 8:
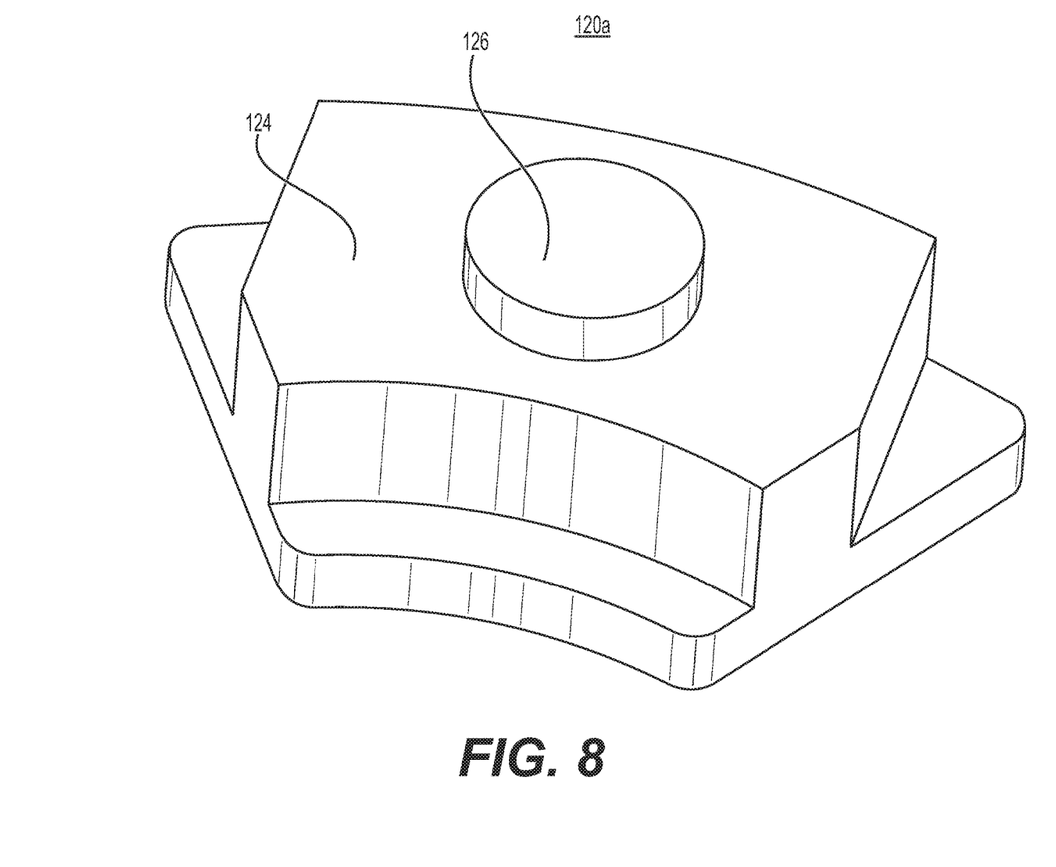
FIG. 8 is a perspective view of a pad illustrating a bottom surface of the pad of the medical device of FIG. 1.

Referring also to FIGS. 7 and 8, a perspective view illustrates a top surface 122 of a pad 120a (FIG. 7) and a perspective view illustrates a bottom surface of the pad 120a (FIG. 8). The pad 120a is shaped and contoured to fit circumferentially around the base ring 102. As discussed above, the pad 120a is configured to engage the base ring in an area 124a defined by a cut-out of the outer wall 242.

The top surface 122 of the pad 120a is generally flat or planar. The pad 120a is contoured and shaped to abut the other pads such that the top surface 122 of all of the pads may form a flat or planar surface that maintains a parallel plane using the action of the lower leveling plates 104a-104f and the upper leveling plates 106a-106f.

The bottom surface of the pad 120a includes a platform area 124 and a raised spherical member 126 in the center of the platform area 124. The platform area 124 covers at least a portion of the entire area of the pad 120a and does not cover the entire area under the top surface 122. While the spherical member 126 is illustrated in this shape in this implementation, other raised shapes may be used in other exemplary implementations.

The spherical member 126 engages a top surface 128 of an upper leveling plate 106a and may exert forces on the top surface 128. The upper leveling plate 106a, in cooperation with the other upper leveling plates and the lower leveling plates 104a-104f act to maintain the pad 120a and the other pads together in a parallel plane.

Figure 9:
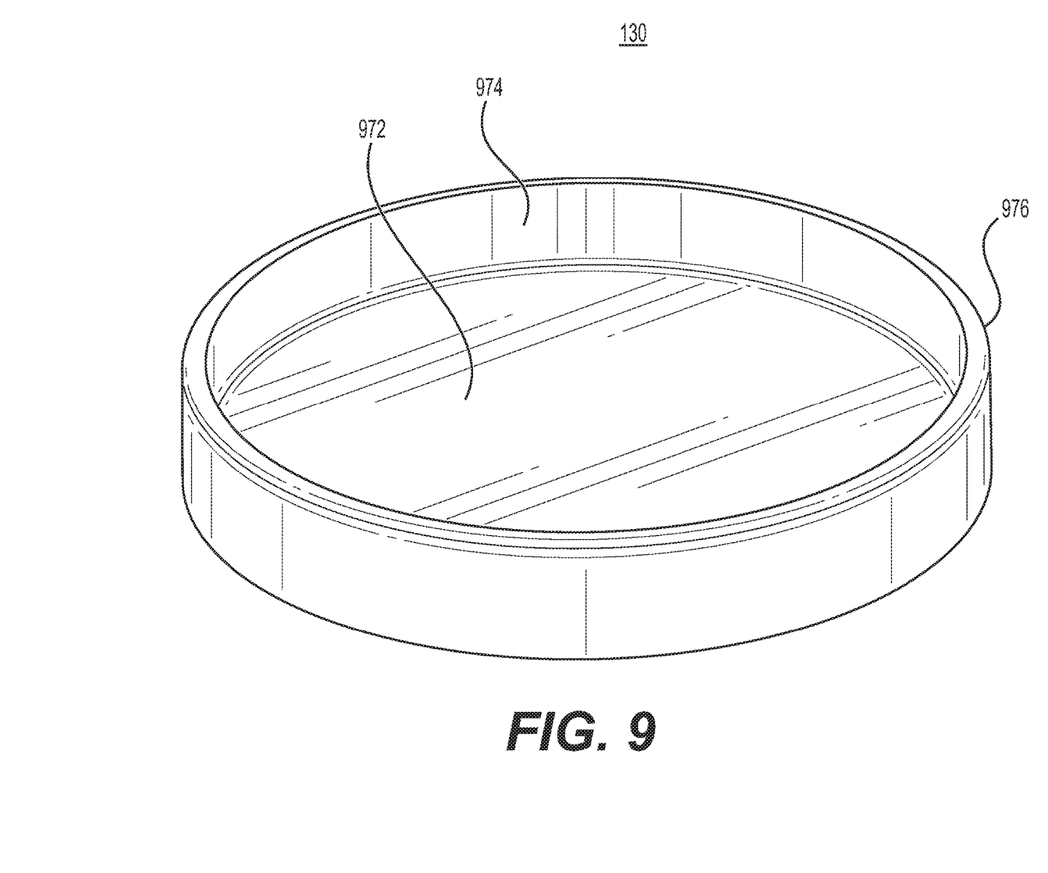
FIG. 9 is a perspective view of a cover illustrating a bottom surface of the cover of the medical device of FIG. 1.
Figure 10:
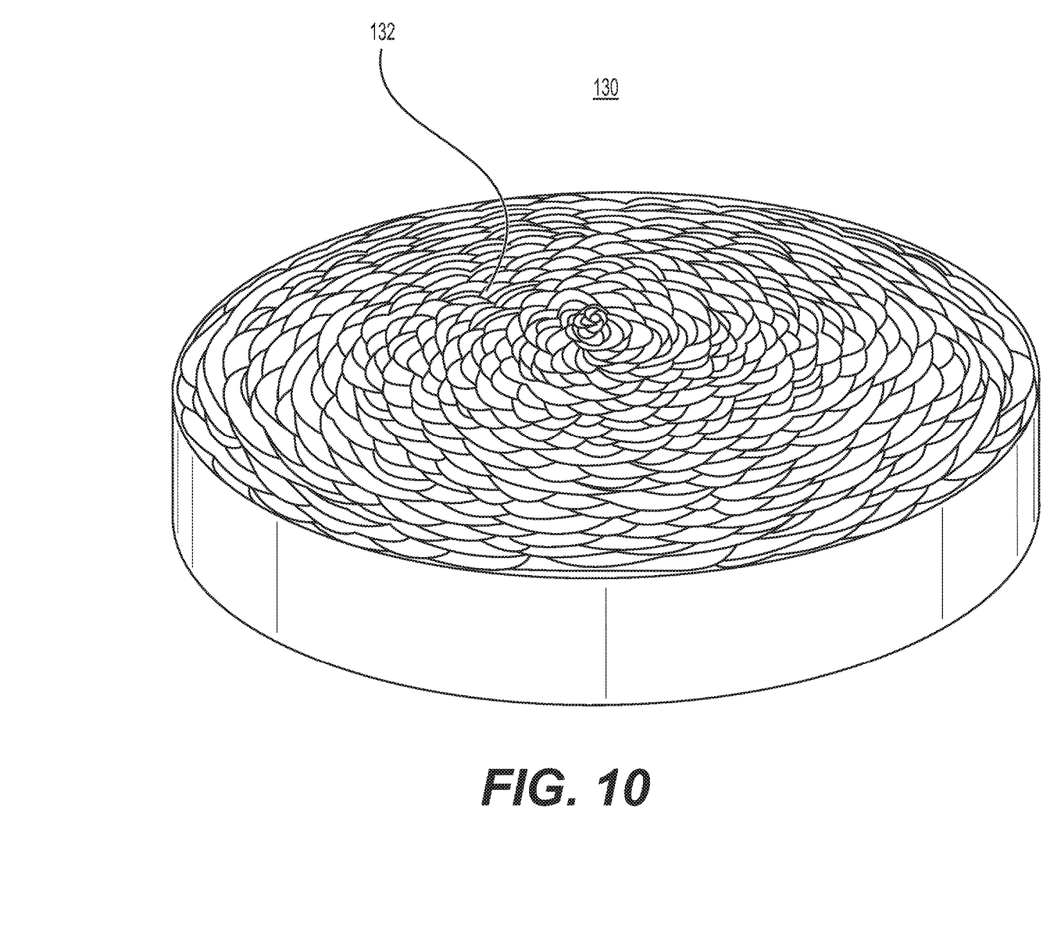
FIG. 10 is a perspective view of a cover illustrating a top surface of the cover of the medical device of FIG. 1.

Referring also to FIGS. 9 and 10, a perspective view illustrates a bottom surface of the cover 130 (FIG. 9) and a perspective view illustrates a top surface 132 of the cover 130 (FIG. 10). The cover 130 may be disc-shaped or spherical-shaped and may be configured to enclose other components of the medical device 100. The cover 130 works in cooperation with the base ring 102 hold the assembly together.

As discussed above, the top surface 132 may function as a contact surface of a vertebrae within a body of a patient. A bottom surface 972 of the cover 130 provides a contact surface for a top of the compressible member 134 to contact. The cover 130 defines a circumferential wall 974 having a lip 976 at the top of the wall 974. The lip 976 may bend or curve slightly inward towards the center of the cover 130 such that when assembled together with the other components of the medical device 100, the lip 976 may hold or at least assist in holding the assembled device together.

Figure 11:
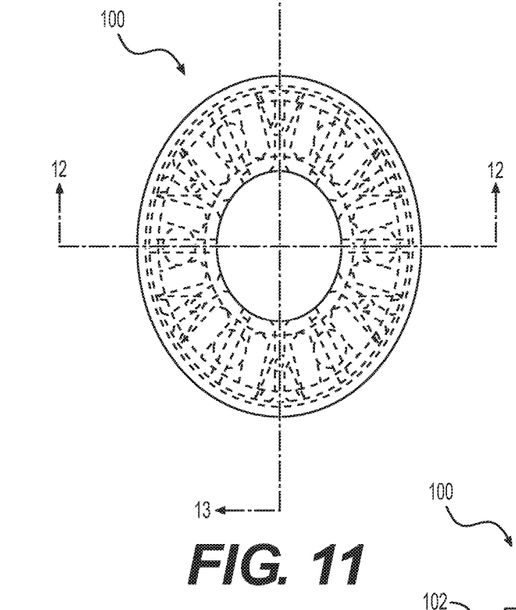
FIG. 11 is a top view shown in cross-section of the medical device of FIG. 1.
Figure 12:
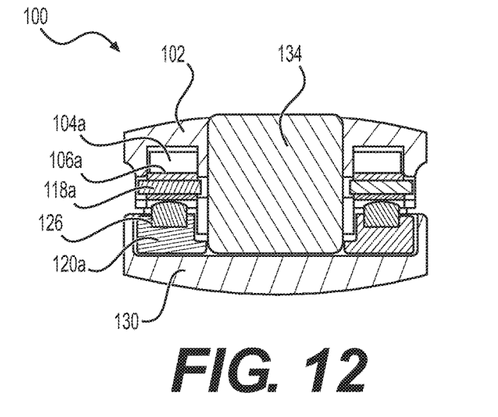
FIG. 12 is a cross-section view along the line A-A of the medical device of view of FIG. 11.
Figure 13:
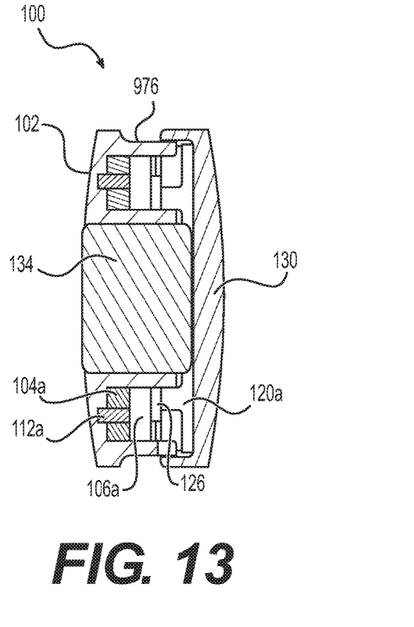
FIG. 13 is a cross-section view along the line B-B of the medical device of view of FIG. 11.

Referring also to FIGS. 11-13, different views of the assembled medical device 100 are illustrated in cross-section. FIG. 11 illustrates a top view of the medical device 100. FIG. 12 illustrates a cross-section view along the line A-A of the view in FIG. 11. FIG. 13 illustrates a cross-section view along the line B-B of the view in FIG. 11.

FIGS. 12 and 13 illustrate the assembled medical device 100. The cross-sections of the medical device 100 illustrate the base ring 102, a lower leveling plate 104a, an upper leveling plate 106a, a pad 120a with a raised spherical member 126 providing force on the upper leveling plate 106a, a cover 130 and a compressible member 134. FIG. 12 illustrates the member 118a extending through the upper leveling plate 106a to maintain the position of the upper leveling plate 106a within the base ring 102. FIG. 13 illustrates the member 112a extending through the lower leveling plate 104a to maintain the position of the lower leveling plate within the base ring 102.

The lip 976 of the cover 130 extends beyond and overlaps with the base ring 102 to hold the assembly together. The cover 130 and the base ring 102 provide contacting surfaces to the vertebrae within the body of the patient.

Figure 14:
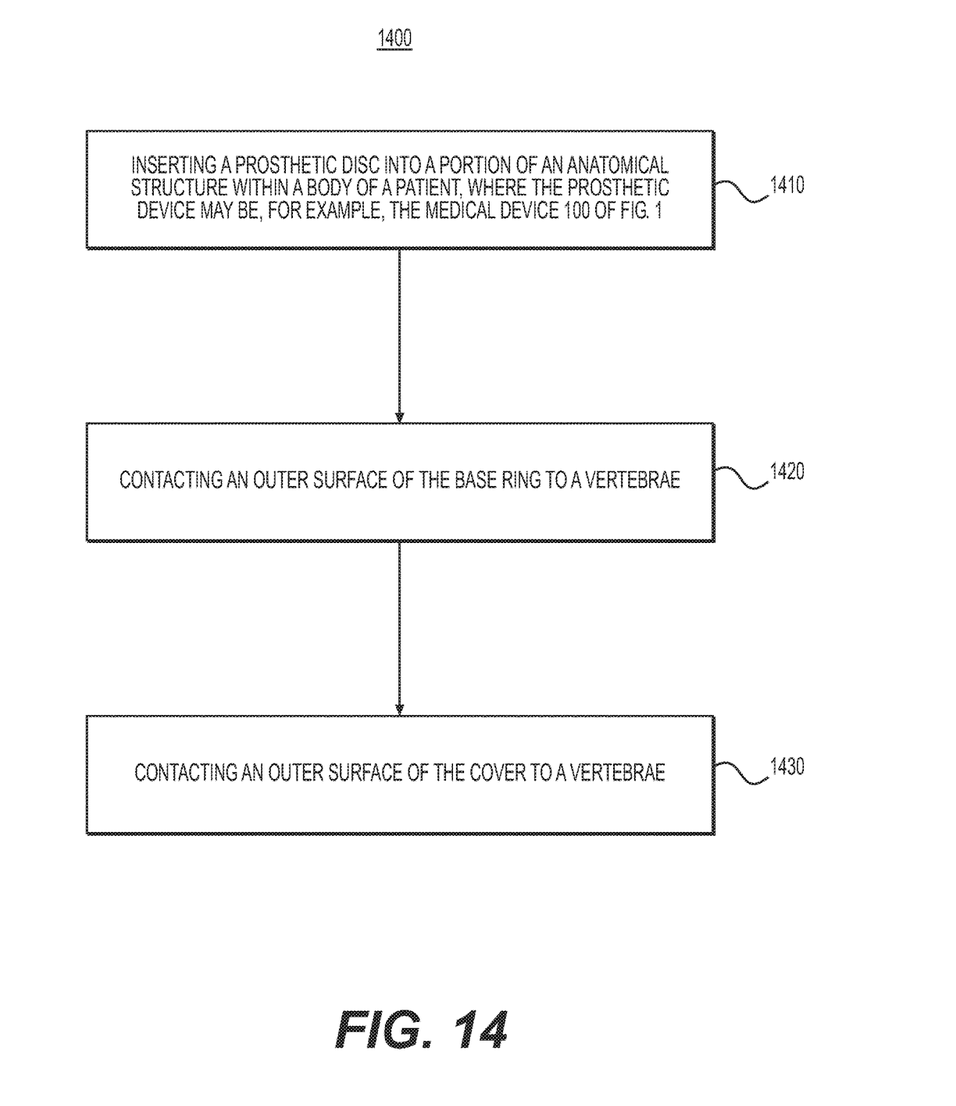
FIG. 14 is a flow chart illustrating an exemplary method including the medical device of FIG. 1.

FIG. 14 is a flow chart illustrating an exemplary process 1400 including the use of the medical device 100. Process 1400 includes inserting a prosthetic disc into a portion of an anatomical structure within a body of a patient (1410). The prosthetic disc may, for example, be the medical device 100 of FIG. 1.

The prosthetic disc may include a base ring (e.g., the base ring 102), multiple layers of multiple leveling plates configured to equalize forces applied to the contact surface of the base ring (e.g., lower leveling plates 104a-104f and upper leveling plates 106a-106f) and a layer of multiple pads with each of the pads having a top surface and a bottom surface (e.g., pads 120a-120f). The top surface of the pads may be configured to maintain a parallel plane and the bottom surface of each of the multiple pads may be configured to engage a top surface of one of the layers of the leveling plates. The prosthetic device may include a cover configured to enclose the multiple layers of the leveling plates, the layer of the multiple pads and the base ring (e.g., cover 130 of FIG. 1).

Process 1400 includes contacting an outer surface of the base ring to a vertebra (1420) and contacting an outer surface of the cover to a vertebra (1430). For example, the contact surface 108 of the base ring 102 may contact a vertebra (1420) and the top surface 132 of the cover 130 may contact a vertebra (1430).

The various components of the medical device 100 described herein can be formed with any biocompatible material used for such a medical device. For example, each of the various components can be formed with one or more biocompatible plastics and/or one or more biocompatible metals such as, for example, titanium and stainless steel.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments. It should be understood that they have been presented by way of example only, not limitation, and various changes in form and details may be made. Any portion of the apparatus and/or methods described herein may be combined in any combination, except mutually exclusive combinations. The embodiments described herein can include various combinations and/or sub-combinations of the functions, components and/or features of the different embodiments described.

What is claimed is:

1. A medical device, comprising:
a base ring configured to contact a first vertebral body;
at least one lower leveling plate, each lower leveling plate configured to engage an inner surface of the base ring;
at least one upper leveling plate, each upper leveling plate configured to engage a top surface of a corresponding lower leveling plate and held in place within the base ring;
a cover configured to enclose the at least one lower leveling plate, the at least one upper leveling plate, and the base ring, wherein the cover is configured to contact a surface of a second vertebral body; and
a compressible member arranged through a center of the at least one lower leveling plate and the at least one upper leveling plate, wherein the compressible member has a top surface configured to engage the cover,
wherein the base ring defines a disc shape, the base ring defining a space between an inner wall and an outer wall, the space between the inner wall and the outer wall configured to receive the at least one lower leveling plate and the at least one upper leveling plate,
wherein the inner wall of the base ring defines an area to receive the compressible member.

2. The medical device of claim 1, further comprising at least one pad having a top surface and a bottom surface, the top surface of each of the at least one pad arranged and configured to maintain a parallel plane and the bottom surface of each of the at least one pad engaging a top surface of a corresponding upper leveling plate.

3. The medical device of claim 2 wherein the top surface of each of the pads is flat and the bottom surface of each of the pads defines a platform having a raised spherical member on a top surface of the platform.

4. The medical device of claim 2, wherein each of the pads maintains the parallel plane using the at least one lower leveling plate and the at least one upper leveling plate.

5. The medical device of claim 1 wherein each of the at least one lower leveling plate and each of the at least one upper leveling plate are configured to equalize and distribute forces applied to a contact surface of the base ring with the first vertebral body and a contact surface of the cover with the second vertebral body.

6. The medical device of claim 1, the at least one lower leveling plate comprises a plurality of lower leveling plates disposed in a manner that is symmetrical about a center of the base ring.

7. The medical device of claim 1 wherein the cover defines a circumferential wall having a lip at a top of the circumferential wall.

8. The medical device of claim 1 wherein the compressible member comprises a biocompatible, flexible material.

9. A medical device, comprising:
a base ring configured to be implanted within a body of a patient;
a layer of lower leveling plates, wherein each lower leveling plate has a non-planar bottom surface that engages an inner surface of the base ring;
a layer of upper leveling plates, respectively corresponding to the layer of lower leveling plates, wherein each upper leveling plate contacts a top surface of a corresponding lower leveling plate; and
a cover disposed in a manner to enclose the base ring, the layer of lower leveling plates, and the layer of upper leveling plates;
wherein a compressible member is disposed in the center of the medical device and engages each of the base ring, the layer of lower leveling plates, the layer of upper leveling plates, and the cover.

10. The medical device of claim 9 wherein the base ring defines a disc shape, the base ring defining a space between an inner wall and an outer wall, the space between the inner wall and the outer wall configured to receive the layer of lower leveling plates and the layer of upper leveling plates.

11. The medical device of claim 10 wherein the inner wall of the base ring defines an area to receive the compressible member.

12. The medical device of claim 9, further comprising a plurality of pads each having a top surface and a bottom surface, the top surface of each of the plurality of pads arranged and configured to maintain a parallel plane and the bottom surface of each of the plurality of pads engaging a top surface of a corresponding upper leveling plate.

13. The medical device of claim 12 wherein the top surface of each of the plurality pads is flat and the bottom surface of each of the plurality of pads defines a platform having a raised spherical member on a top surface of the platform.

14. The medical device of claim 12 wherein each of the plurality of pads maintains the parallel plane using the layer of lower leveling plates and the layer of the upper leveling plates.

15. The medical device of claim 9 wherein the layer of lower leveling plates and the layer of upper leveling plates are configured to equalize and distribute forces applied to the base ring and the cover from adjacent vertebral bodies.

16. The medical device of claim 9, the layer of lower leveling plates is disposed in a manner that is symmetrical about a center of the base ring.

17. The medical device of claim 9 wherein the cover defines a circumferential wall having a lip at a top of the circumferential wall.

18. The medical device of claim 9 wherein the compressible member comprises a biocompatible, flexible material.

* * * * *